(12) United States Patent
Kucmierczyk et al.

(10) Patent No.: US 11,365,171 B2
(45) Date of Patent: *Jun. 21, 2022

(54) PROCESS FOR PREPARING AN ESTER BY ALKOXYCARBONYLATION

(71) Applicant: Evonik Operations GmbH, Essen (DE)

(72) Inventors: Peter Kucmierczyk, Herne (DE); Robert Franke, Marl (DE); Dirk Fridag, Haltern am See (DE); Johannes Knossalla, Schermbeck (DE); Marc Schäpertöns, Recklinghausen (DE); Frederik Gluth, Mülheim an der Ruhr (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/893,463

(22) Filed: Jun. 5, 2020

(65) Prior Publication Data

US 2020/0392064 A1    Dec. 17, 2020

(30) Foreign Application Priority Data

Jun. 12, 2019 (EP) .................... 19179570

(51) Int. Cl.
| | |
|---|---|
| *C07C 67/02* | (2006.01) |
| *B01D 61/24* | (2006.01) |
| *B01D 71/52* | (2006.01) |
| *B01J 23/44* | (2006.01) |
| *C07C 67/31* | (2006.01) |
| *C07C 67/38* | (2006.01) |
| *C07C 67/48* | (2006.01) |

(52) U.S. Cl.
CPC ............ *C07C 67/02* (2013.01); *B01D 61/246* (2013.01); *B01D 71/52* (2013.01); *B01J 23/44* (2013.01); *C07C 67/31* (2013.01); *C07C 67/38* (2013.01); *C07C 67/48* (2013.01)

(58) Field of Classification Search
CPC ......... C07C 67/02; C07C 67/31; C07C 67/38; C07C 67/48; C07C 69/24; C07C 67/03; C07C 67/56; C07C 51/09; C07C 53/128; B01D 61/246; B01D 71/52; B01D 61/027; B01J 23/44
See application file for complete search history.

(56) References Cited

U.S. PATENT DOCUMENTS

| | | | |
|---|---|---|---|
| 3,987,089 A * | 10/1976 | Slejko ..................... B01J 23/56 554/127 |
| 9,676,805 B2 | 6/2017 | Dyballa et al. |
| 9,688,604 B2 | 6/2017 | Jennerjahn et al. |
| 9,725,398 B2 | 8/2017 | Dong et al. |
| 9,845,276 B2 | 12/2017 | Franke et al. |
| 10,077,228 B2 | 9/2018 | Dong et al. |
| 10,155,200 B2 | 12/2018 | Geilen et al. |
| 10,202,329 B2 | 2/2019 | Dong et al. |
| 10,245,578 B2 | 4/2019 | Klasovsky et al. |
| 10,294,191 B2 | 5/2019 | Dong et al. |
| 10,501,392 B2 | 12/2019 | Fridag et al. |
| 10,562,833 B2 | 2/2020 | Fridag et al. |
| 10,577,297 B2 | 3/2020 | Fridag et al. |
| 10,633,302 B2 | 4/2020 | Nadolny et al. |
| 10,647,650 B2 | 5/2020 | Hecht et al. |
| 10,654,784 B2 | 5/2020 | Hasselberg et al. |
| 2009/0012323 A1 | 1/2009 | Van Rensburg et al. |
| 2016/0236150 A1 * | 8/2016 | Geilen ................. B01J 31/4061 |
| 2016/0257634 A1 | 9/2016 | Dyballa et al. |
| 2017/0022138 A1 | 1/2017 | Dong et al. |
| 2019/0283003 A1 | 9/2019 | Nadolny et al. |
| 2019/0283004 A1 | 9/2019 | Nadolny et al. |
| 2019/0283005 A1 | 9/2019 | Nadolny et al. |

FOREIGN PATENT DOCUMENTS

| | | | |
|---|---|---|---|
| EP | 0321054 | * | 6/1989 |
| EP | 3 121 184 A2 | | 1/2017 |
| WO | 2013/107902 A1 | | 7/2013 |
| WO | WO2013/107902 | * | 7/2013 |
| WO | 2015/110843 A1 | | 7/2015 |
| WO | WO2015110843 | * | 7/2015 |

OTHER PUBLICATIONS

Kucmierczyk et al., U.S. Appl. No. 16/893,481, filed Jun. 5, 2020.
Marchetti et al., "Molecular Separation with Organic Solvent Nanofiltration: A Critical Review," Chemical Reviews, Copyright Oct. 2014, Bd. 114, Nr. 21, pp. 10735-10806 (72 pages).
Kucmierczyk et al., U.S. Appl. No. 16/888,920, filed Jun. 1, 2020.
Kucmierczyk et al., U.S. Appl. No. 16/888,925, filed Jun. 1, 2020.

* cited by examiner

Primary Examiner — Yevgeny Valenrod
Assistant Examiner — Blaine G Doletski
(74) Attorney, Agent, or Firm — Taylor English Duma LLP; Philip P. McCann

(57) ABSTRACT

The invention relates to a process for preparing an ester by alkoxycarbonylation of a C2 to C20 hydrocarbon having at least one multiple bond, preferably having at least one olefinic double bond, in which the homogeneous catalyst system used is separated from the product mixture by means of membrane separation and recycled into the reaction zone. In a development of the present invention, the ester thus formed is converted into another ester by transesterification.

18 Claims, No Drawings

PROCESS FOR PREPARING AN ESTER BY ALKOXYCARBONYLATION

CROSS REFERENCE TO RELATED APPLICATIONS

This application is a 35 U.S.C. § 119 patent application which claims the benefit of European Application No. 19179570.7 filed Jun. 12, 2019, which is incorporated herein by reference in its entirety.

FIELD

The present invention relates to a process for preparing an ester by alkoxycarbonylation of a C2 to C16 hydrocarbon having at least one multiple bond, preferably having at least one olefinic double bond, in which the homogeneous catalyst system used is separated from the product mixture by means of membrane separation and recycled into the reaction zone. In a development of the present invention, the ester thus formed is converted into another ester by trans-esterification.

BACKGROUND

Alkoxycarbonylation is the reaction of a hydrocarbon that has at least one multiple bond, preferably at least one olefinic double bond, with carbon monoxide and an alcohol to form the corresponding esters. This is normally done using metal-ligand complexes as catalysts, which are present in homogeneous solution in the reaction mixture and thus in the product mixture too. In order to be able to isolate the desired ester from the product mixture, it is advantageous to first remove from the product mixture at least the major portion of the homogeneously dissolved catalyst. On the other hand, the costs of the catalysts used are comparatively high, which is why the catalyst should also be recovered not least on economic grounds.

Various processes are known for separating the homogeneously dissolved catalyst from the rest of the reaction mixture. WO 2013/107902 A1 discloses, by way of example, a process in which the homogeneously dissolved catalyst is separated after the alkoxycarbonylation by means of a membrane that is impermeable to molecules having a molecular weight of 1 kDa and above, with the result that the catalyst is retained and enriched in the retentate. According to WO 2013/107902 A1, preference is given to membrane materials based on polyimides or polydimethylsiloxane.

However, the materials disclosed in WO 2013/107902 A1 have the disadvantage that they often do not have adequate long-term stability, particularly towards acids, which as co-catalysts typically form part of the catalyst system, and can become unstable when subjected to multiple loads. Moreover, these membrane materials do not show any appreciable retention for the hydrocarbon used or the solvent, which may at the same time be a reactant in the alkoxycarbonylation, for example the alcohol used. Neither alcohol nor hydrocarbon are enriched in the retentate. This means that more elaborate downstream workup and/or purification steps, such as subsequent distillation steps, are necessary in order to separate the solvent/reactants from the product.

SUMMARY

The object of the present invention was accordingly to provide an alkoxycarbonylation process in which the homogeneous catalyst is separated using an acid-stable membrane material that may also be used for a relatively long period of time. The object was additionally to provide an alkoxycarbonylation process in which the products formed pass through preferentially during membrane separation, with at least partial retention of at least a proportion of the reactants used, in particular the alcohol.

The object underlying the present invention was able to be achieved by the process according to Claim 1. Preferred embodiments are specified in the dependent claims.

DETAILED DESCRIPTION

According to the invention, the process for preparing an ester comprises carbonylation of a C2 to C16 hydrocarbon, with the process comprising the following steps:

a) reacting (carbonylating) a C2 to C16 hydrocarbon having at least one olefinic double bond with carbon monoxide and with an alcohol that is a mono- or polyol (two or more OH groups) having 1 to 50 carbon atoms or is a mixture of two or more mono- and/or polyols and which, when it is a monool, is used in a molar ratio to the C2 to C16 hydrocarbon (alcohol:C2 to C16 hydrocarbon) of 2 to 20 or which, when it is a polyol, is used in a molar ratio to the hydrocarbon used (hydrocarbon:polyol) of 2 to 20, in the presence of a homogeneous catalyst system comprising at least one metal of groups 8 to 10 of the periodic table of the elements or a compound thereof, a phosphorus-containing ligand and an acid, in a reaction zone to obtain a liquid product mixture that comprises at least the ester formed by the reaction, the homogeneous catalyst system, low boilers and/or high boilers and unreacted alcohols;

b) carrying out a membrane separation to separate the homogeneous catalyst system from the liquid product mixture, whereby the homogeneous catalyst system and additionally unreacted hydrocarbon and/or unreacted alcohol, preferably unreacted alcohol, are enriched in the retentate and the ester formed in step a) is enriched in the permeate, wherein the membrane material used is an OSN (organic solvent filtration) membrane material that is acid-stable, i.e. stable in the presence of the acid of the catalyst system for at least 300 h, and has at least one surface-active layer, and the retentate is recycled into the reaction zone;

c) working up the permeate by means of one or more separation steps selected from thermal separation, extraction, crystallization or membrane separation, preferably by means of one or more distillation steps, for removing the ester formed in step a) and for removing the unreacted C2 to C16 hydrocarbon having at least one olefinic double bond and/or the unreacted alcohol and recycling of the unreacted C2 to C16 hydrocarbon having at least one olefinic double bond and/or the unreacted alcohol into the reaction zone of step a.

The hydrocarbons used in the reaction in step a) must have at least one multiple bond. Preference is given to hydrocarbons having at least one olefinic double bond and particular preference to hydrocarbons having one olefinic double bond. There is in principle no limit to the number of carbon atoms in the compound having at least one multiple bond, preferably at least one olefinic double bond. However, only the carbonylation of C2 to C16 hydrocarbons having at least one multiple bond, preferably at least one olefinic double bond, is industrially relevant. In a preferred embodiment of the present invention, C3 to C12 hydrocarbons having preferably at least one olefinic double bond may be used. These include in particular n-alkenes, isoalkenes, cycloalkenes and aromatic alkenes having 2 to 16 carbon atoms, preferably 3 to 12 carbon atoms.

The hydrocarbons described above may contain one or more further functional groups in addition to the at least one olefinic double bond. Examples of suitable functional groups are carboxyl, thiocarboxyl, sulfo, sulfinyl, carboxylic anhydride, imide, carboxylic ester, sulfonic ester, carbamoyl, sulfamoyl, cyano, carbonyl, carbonothioyl, hydroxyl, sulfhydryl, amino, ether, thioether, aryl, heteroaryl or silyl groups and/or halogen substituents.

Particularly preferred hydrocarbons used in step a) of the process according to the invention have only one olefinic double bond, in particular n-alkenes and isoalkenes having 2 to 16 carbon atoms, preferably 3 to 12 carbon atoms. The hydrocarbons used are preferably unsubstituted.

The employed and above-described hydrocarbons having an olefinic double bond are according to the invention reacted in step a) with carbon monoxide (CO) and an alcohol to form the corresponding ester. The carbon monoxide may be provided directly as a feed mixture or by adding a carbon monoxide-containing gas selected from synthesis gas, water gas, generator gas and other carbon monoxide-containing gases. It is also possible to provide the carbon monoxide by first separating the carbon monoxide-containing gas into its components in a manner known to those skilled in the art and passing the carbon monoxide into the reaction zone. The carbon monoxide may still contain a certain proportion of hydrogen or other gases, because complete separation is almost impossible.

The alcohol used in the reaction in step a) is a mono- or polyol (two or more OH groups) having 1 to 50 carbon atoms, preferably 1 to 15 carbon atoms, more preferably 1 to 10 carbon atoms, or a mixture of two or more mono- and/or polyols. In a preferred embodiment, the polyol is a diol, triol or tetraol, preferably a diol or triol, having the abovementioned number of carbon atoms. Suitable alcohols for the reaction in step a) are methanol, ethanol, 1-propanol, 1-butanol, 1-pentanol, 1-hexanol, 2-propanol, tert-butanol, 3-pentanol, 2-propylheptanol, cyclohexanol, phenol or mixtures thereof, preferably ethanol, 1-propanol, 1-butanol, 1-pentanol, 1-hexanol, 2-propanol, tert-butanol, 3-pentanol, 2-propylheptanol.

The alcohol used in step a), when it is a monool, is used in a molar ratio to the hydrocarbon used (monool:hydrocarbon) of 2 to 20, preferably of 3 to 10 and more preferably of 4 to 6. The monool is thus added in a molar excess based on the hydrocarbon used. The alcohol may accordingly serve both as a reactant for the carbonylation and as solvent. The alcohol used in step a), when it is a polyol, is used in a molar ratio to the hydrocarbon used (hydrocarbon:polyol) of 2 to 20, preferably of 3 to 10 and more preferably of 4 to 8. The polyol is thus added in a molar deficit based on the hydrocarbon used.

The reaction according to the invention in step a) is carried out in the presence of a homogeneous catalyst system that comprises at least one metal from groups 8 to 10 of the periodic table of the elements (PTE) or a compound thereof, a phosphorus-containing ligand and an acid as co-catalyst.

The metal from groups 8 to 10 of the PTE is preferably palladium. The palladium is preferably used in the form of a precursor compound as a palladium compound coordinated by the phosphorus-containing ligand. Examples of palladium compounds that may be used as precursor compounds are palladium chloride [$PdCl_2$], palladium(II) acetylacetonate [$Pd(acac)_2$], palladium(II) acetate [$Pd(OAc)_2$], dichloro(1,5-cyclooctadiene)palladium(II) [$Pd(cod)Cl_2$], bis (dibenzylideneacetone)palladium(0) [$Pd(dba)_2$], tris(dibenzylideneacetone)dipalladium(0) [$Pd_2(dba)_3$] bis(acetonitrile)dichloropalladium(II) [$Pd(CH_3CN)_2Cl_2$], palladium (cinnamyl)dichloride [$Pd(cinnamyl)Cl_2$]. Preference is given to using the compounds [$Pd(acac)_2$] or [$Pd(OAc)_2$]. The concentration of palladium metal in step a) is preferably between 0.01 and 0.6 mol %, preferably between 0.03 and 0.3 mol %, more preferably between 0.04 and 0.2 mol %, based on the molar amount of the hydrocarbon used.

Suitable phosphorus-containing ligands of the catalyst system according to the invention preferably have a bidentate structure. Preferred phosphorus-containing ligands for the catalyst system according to the invention are benzene-based diphosphine compounds, as disclosed, for example, in EP 3 121 184 A2. The ligands may be combined with the palladium in a preliminary reaction so that the palladium-ligand complex is fed into the reaction zone or added to the reaction in situ and combined with the palladium there. The molar ratio of ligand to metal for the reaction described in step a) may be 1:1 to 10:1, preferably 2:1 to 6:1, more preferably 3:1 to 5:1.

The homogeneous catalyst system further comprises an acid, in particular a Brønsted or a Lewis acid. Lewis acids used may in particular be Lewis acids having an LAU value of more than 25, preferably having an LAU value of 29. The LAU value is a new method of determining the strength of Lewis acids (JR Gaffen et al., Chem, vol. 5, issue 6, p. 1567-1583). Lewis acids used are preferably aluminium triflate, aluminium chloride, aluminium hydride, trimethylaluminium, tris(pentafluorophenyl)borane, boron trifluoride, boron trichloride or mixtures thereof. Of the Lewis acids mentioned, preference is given to using aluminium triflate. The Lewis acid is preferably added in a molar ratio of Lewis acid to ligand of 1:1 to 20:1, preferably 2:1 to 15:1, more preferably 5:1 to 10:1.

Suitable Brønsted acids preferably have an acid strength pKa of ≤5, more preferably an acid strength pKa of ≤3. The stated acid strength pKa refers to the pKa determined under standard conditions (25° C., 1.01325 bar). For polyprotic acids, the acid strength pKa in the context of this invention relates to the pKa of the first protolysis step. The Brønsted acid is preferably added in a molar ratio of Brønsted acid to ligand of 1:1 to 15:1, preferably 2:1 to 10:1, more preferably 3:1 to 5:1.

The Brønsted acid used may in particular be perchloric acid, sulfuric acid, phosphoric acid, methylphosphonic acid or sulfonic acids. Examples of suitable sulfonic acids are methanesulfonic acid, trifluoromethanesulfonic acid, tert-butanesulfonic acid, p-toluenesulfonic acid (PTSA), 2-hydroxypropane-2-sulfonic acid, 2,4,6-trimethylbenzenesulfonic acid and dodecylsulfonic acid. Particularly preferred acids are sulfuric acid, methanesulfonic acid, trifluoromethanesulfonic acid and p-toluenesulfonic acid. The acid is preferably sulfuric acid. The reaction/carbonylation in step a) of the employed hydrocarbon having an olefinic double bond is preferably carried out at a temperature of 25 to 140° C., more preferably at a temperature of 80 to 130° C. and particularly preferably at a temperature of 90 to 120° C. The pressure in step a) may be between 5 and 60 bar, preferably between 10 and 40 bar, more preferably between 15 and 30 bar.

The described reaction in step a) takes place in a suitable reaction zone. The reaction zone for the reaction comprises at least one reactor, but may also consist of two or more reactors. The at least one reactor may in particular be selected from the group consisting of a stirred-tank reactor, a loop reactor, a jet-loop reactor, a bubble-column reactor or combinations thereof. If more than one reactor is used, the reactors may be identical or different.

The above-described reaction in step a) affords a liquid product mixture comprising at least the ester formed by the reaction, the homogeneous catalyst system, unreacted alcohols A, and possibly further components such as low boilers, for example low-boiling by-products such as ethers, and/or high boilers and/or unreacted hydrocarbons. The product mixture is then fed into the subsequent membrane separation in step b). In the reaction in step a), an offgas that consists at least of unreactive impurities such as nitrogen, hydrogen, alkanes and low-boiling by-products (for example the ethers already mentioned) may also be removed from the reaction zone. The impurities and low-boiling by-products could accumulate and, over time, lower the partial pressure of the reaction gas (CO), thereby slowing down the reaction.

In step b) that follows, the product mixture is fed into a membrane separation to separate the homogeneous catalyst system from the product mixture. The membrane material according to the invention causes enrichment in the retentate of the homogeneous catalyst system and unreacted hydrocarbon and/or unreacted alcohol, whereas the ester formed in step a) is enriched in the permeate. The permeate containing the ester formed is then fed into the subsequent step c). The retentate containing the enriched homogeneous catalyst system is then recycled into the reaction zone. On recycling the retentate, a purge stream that may contain inert alkanes, low-boiling by-products (for example ethers), possible decomposition products of the catalyst system or other impurities introduced by the hydrocarbon streams used, for example traces of water or nitrogen, may additionally be removed to avoid accumulation in the reaction zone(s). The recycling of the retentate ensures that the catalyst system obtained in the retentate in the membrane separation is returned to the reaction. This minimizes catalyst losses through deposition or deactivation and makes the process more cost-efficient. Catalyst losses usually cannot be avoided entirely, but the effect of the decrease in the losses mentioned is that less catalyst has to be replaced by supply of fresh catalyst.

Membrane separation is based on the semipermeability of the membrane material, which is permeable to certain substances and impermeable to others. The membrane material used in step b) of the process according to the invention is an OSN membrane material (OSN=organic solvent nanofiltration). Such a membrane material preferably consists at least of a relatively thin separation-active layer (also: active separation layer) and optionally a thicker backing on which the separation-active layer is located. The membrane material according to the invention preferably consists at least of a separation-active layer and a backing. One or more intermediate layers may be present between the separation-active layer and the backing. In a preferred embodiment, the membrane material consists solely of the separation-active layer and the backing. The membrane material, composed at least of separation-active layer and backing, should be acid-stable so that the membrane material is not damaged by the acid present as co-catalyst in the liquid product mixture. The term "acid-stable" in the context of the present invention means that the membrane material is stable and is not destroyed for at least 300 h in the presence of the acid in the catalyst system, especially a Brønsted acid having a pKa ≤5, more preferably having a pKa ≤3, or a Lewis acid having an LAU value of more than 25, preferably having an LAU of 29, as a result of which the actual separating action could no longer be achieved.

In particular, the backing has a porous structure that is permeable to the permeate that has passed through the separation-active layer. The backing has a stabilizing function and serves as a support for the separation-active layer. The backing may in principle be composed of any suitable porous material. A prerequisite, however, is that the material is stable to acids and bases. The backing may consist of the same material as the separation-active layer.

The separation-active layer according to the invention is preferably composed of a PAEK (polyaryl ether ketone) polymer. PAEK has the particular feature that, within the repeat unit, aryl groups are linked alternately via an ether functionality and a ketone functionality. A separation-active layer that is preferred according to the invention is composed of PEEK (polyether ether ketone). As the separation-active layer, particular preference is given to using PEEK polymers having a degree of sulfonation of less than 20%, particularly preferably having a degree of sulfonation of less than 10%. The corresponding PEEK polymers and the preparation thereof are described in WO 2015/110843 A1 or in J. da Silva Burgal et al.; Journal of Membrane Science, vol. 479 (2015), pp. 105-116. This material has surprisingly been found to be particularly stable, particularly also towards the acid co-catalyst of the homogeneous catalyst system. In addition, a particular feature of the PEEK material according to the invention is that, when used as a separation-active layer, it allows the esters that are formed to pass through preferentially, whereas even the alcohols used as reactants are at least partially retained and thereby accumulate in the retentate. This allows the subsequent processing of the residual liquid product mixture to be carried out more economically and for longer, because less alcohol needs to be removed compared with known membrane materials.

The membrane separation in step b) is carried out preferably at a temperature of 25 to 100° C., more preferably 30 to 80° C. and particularly preferably 40 to 70° C. To bring the product mixture to the prevailing temperature preferred for the membrane separation, the product mixture may be cooled. In addition to active cooling using a coolant, cooling may also be achieved via a heat exchanger, whereby another stream is heated within the process according to the invention. Optionally, there is also a degassing step between the reaction zone in step a) and the membrane separation in step b) in order to remove volatile compounds such as carbon monoxide and/or residual unreacted impurities that have not been removed via the offgas, such as nitrogen, hydrogen, alkanes and low-boiling by-products (for example the ethers already mentioned) from the product mixture beforehand. The product mixture is first depressurized below the partial pressure of the dissolved components, such as carbon monoxide, so that they are displaced from solution, thereby allowing the pressure to then be raised again as specified for the membrane separation.

The transmembrane pressure (TMP) in step b) may be 10 to 60 bar, preferably 15 to 55 bar, more preferably 20 to 50 bar (relative). The permeate-side pressure may here be above atmospheric pressure up to 15 bar, preferably 3 to 7 bar, which then gives rise to the retentate-side pressure brought about by the TMP. In a preferred embodiment, care should be taken, in the case of the pressure ratios and the permeate-side pressure in particular, to ensure that the pressure is set according to the hydrocarbon used, the alcohol used and the temperature in the system, in order to avoid evaporation after passage through the membrane, since this could make the entire operation unstable. The same applies in principle also to dissolved components such as carbon monoxide, which may optionally be removed by the degassing step already mentioned.

The economics of membrane separation processes can be substantially determined by the service life of the membrane materials used, which is why the service life/stability of the membrane can likewise be a criterion for selecting the suitable membrane material. A minimum service life of about half a year is assumed. This can be particularly relevant for processes, such as the present process, in which the product is enriched in the permeate, because the membrane surface area needed increases with the total capacity of the process.

This results in three criteria in particular for the service life/stability of the membrane, these being the technical integrity of the membrane, the membrane retention (corresponding to the separation performance of the membrane, see definition below) and the permeability of the membrane (see definition below). Defects concerning the technical integrity, such as dissolution of the membrane, the formation of imperfections or holes or significant shrinkage or enlargement of the membrane surface area, may be reflected in the retention of the membrane (retention decreases) and the permeability (permeability increases), as well as ensuring that the membrane can no longer be pressurized to the specified pressure and/or that the transmembrane pressure cannot be set.

For characterization of the permeability or separation performance of a membrane in membrane technology, the retention R of the membrane in respect of a specific component of the substance mixture is defined according to the following formula (1):

$$R = 1 - w_{(i)P}/w_{(i)R} \qquad (1),$$

where $w_{(i)P}$ represents the mass fraction of the relevant component in the permeate and $w_{(i)R}$ the mass fraction of the relevant component in the membrane retentate. The retention may thus have a value from 0 to 1 and is therefore preferentially stated in %. A retention of 0% means that the relevant component permeates unhindered through the membrane, with the result that the mass fractions of the components in the retentate are the same as in the permeate. Conversely, a retention of 100% means that the relevant component is retained completely by the membrane, but this is almost impossible industrially.

In addition to the retention, the so-called permeability of the membrane is also key to the characterization of its permeability according to the following formula (2):

$$P = m'/(A*TMP) \qquad (2),$$

where m' represents the mass flow rate of the permeate, A the surface area of the membrane and TMP the applied transmembrane pressure. The permeability is usually stated in units of kg/(h*m²*bar). Permeability is thus a characteristic normalized to the membrane surface area and the TMP established.

As regards characterization of the stability of a membrane, a relative change in the permeability $P_{Rel}$ can be defined according to the following formula (3):

$$P_{Rel} = P_{t=x}/P_{t=0} \qquad (3),$$

where $P_{t=x}$ represents the permeability at time t=x and $P_{t=0}$ the original permeability at time t=0 (a different reference time is also possible, with the proviso that t=x>t=y).

A membrane can additionally be characterized via the selectivity for a particular component. The selectivity describes the ratio of the concentrations of a particular component i before and after the membrane. The selectivity is calculated according to formula (4) below:

$$S_i = C_{P\_i}/C_{F\_i} \qquad (4),$$

where $C_{F\_i}$ represents the concentration of the relevant component i in the feed to the membrane, in this case the liquid product mixture, and $C_{P\_i}$ represents the concentration of the relevant component i in the permeate.

In a preferred embodiment of the present invention, after being used for 300 hours in the membrane separation process in step b) described herein, the membrane material according to the invention exhibits the following two characteristics:

the membrane retention R for the homogeneous catalyst system is at least 75%, preferably 85%, more preferably 90%, and worsens by not more than 30 percentage points, preferably not more than 20 percentage points, more preferably not more than 10 percentage points;

or the relative permeability $P_{rel}$ has a value between 30% and 300%, preferably between 50% and 150%, more preferably between 75% and 125%.

The membrane should accordingly not lose its technical integrity. Examples of loss of technical integrity are dissolution of the membrane, the formation of defects/holes and/or significant shrinkage or a considerable increase in the membrane surface area. The membrane material according to the invention should in particular be stable to the presence of acids in an amount of 0.1% by weight to 5% by weight, not lose its technical integrity and exhibit the two characteristics mentioned above.

In the subsequent step c), to separate the esters formed in step a) from the remaining permeate, the permeate from the membrane separation (step b)) is subjected to a separation process selected from the group consisting of a thermal separation, for example distillation, extraction, crystallization or a further membrane separation. The separation process is preferably a distillation. The appropriate process conditions are known to those skilled in the art.

In the separation process used in step c) and in the distillation in particular, there is the possibility that this separates from the permeate not just the ester that is formed, but high boilers that have possibly formed too, for example high-boiling by-products that can arise in the reaction in step a). In order to remove these high boilers, the process according to the invention may include a purification step, i.e. a step in which the ester formed is purified by separating the ester from high boilers present in the permeate by means of a thermal separation, extraction, crystallization or membrane separation. Preferably a thermal separation process, more preferably a further distillation, is used to purity the esters formed. The process conditions are known to those skilled in the art.

In a preferred embodiment, the permeate obtained in step c), which is largely free of the ester formed in step a) and comprises at least unreacted alcohols and/or unreacted hydrocarbons, undergoes a separation of recyclable components. In this separation, the unreacted alcohols and/or unreacted hydrocarbons are separated from the remaining permeate, in particular from the low boilers contained therein, by means of a thermal separation, extraction, crystallization or membrane separation. Preferably a thermal separation process, more preferably a further distillation, is used to separate the unreacted alcohols and/or unreacted hydrocarbons from the remaining permeate. The process conditions are known to those skilled in the art. The unreacted alcohols and/or unreacted hydrocarbons obtained here may then be recycled into the reaction zone.

The ester formed by the process according to the invention may be transesterified in two further subsequent process steps d) and e). In this transesterification, the part of the ester that corresponds to the first alcohol used in step a) is replaced by a second alcohol. This transesterification is carried out after step c) mentioned above, optionally after the possible purification step, and comprises the following steps:

d) transesterifying the ester formed in step a) with a second alcohol, wherein this second alcohol differs from the alcohol used in step a), in a second reaction zone to obtain a second product mixture comprising at least the ester with the second alcohol, the eliminated first alcohol and unreacted second alcohol;

e) separating the ester formed with the second alcohol from the rest of the second product mixture and in particular from the eliminated first alcohol by means of one or more separation steps selected from thermal separation, extraction, crystallization or membrane separation, preferably by thermal separation and/or by means of membrane separation, more preferably by means of one or more distillation steps, and recycling of the eliminated first alcohol into the first reaction zone from step a) and recycling of the unreacted second alcohol into the second reaction zone.

Step d) is where the actual transesterification takes place, that is to say the elimination of the first alcohol actually attached in step a) and the attachment of the second alcohol. In this step, the ester formed in step a) is reacted in a reaction zone with a second alcohol that differs from the first alcohol. In a particularly preferred embodiment, the second alcohol used in the transesterification is a higher-boiling alcohol compared with the first alcohol used in step a). In order to favor the transesterification reaction, the second alcohol is preferably added in excess in the transesterification.

The second alcohol used in the transesterification in step d) is preferably a mono- or polyol (two or more OH groups) having 1 to 50 carbon atoms, more preferably having 1 to 15 carbon atoms, particularly preferably having 1 to 10 carbon atoms, or a mixture of two or more mono- and/or polyols, with the proviso that the first alcohol used in step a) and the second alcohol are non-identical. In a preferred embodiment, the polyol is a diol, triol or tetraol, preferably a diol or triol, having the abovementioned number of carbon atoms. Suitable alcohols for the reaction in step a) are methanol, ethanol, 1-propanol, 1-butanol, 1-pentanol, 1-hexanol, 2-propanol, tert-butanol, 3-pentanol, 2-propylheptanol, cyclohexanol, phenol, pentaerythritol, neopentyl glycol, trimethylolpropane, dipentaerythritol or mixtures thereof, preferably ethanol, 1-propanol, 1-butanol, 1-pentanol, 1-hexanol, 2-propanol, tert-butanol, 3-pentanol, 2-propylheptanol.

The transesterification in step d) is preferably carried out under acid or base catalysis. The acids used may be Brønsted or Lewis acids.

Suitable Brønsted acids for the transesterification in step d) are perchloric acid, sulfuric acid, phosphoric acid, methylphosphonic acid or a sulfonic acid, for example methanesulfonic acid, trifluoromethanesulfonic acid, tert-butanesulfonic acid, p-toluenesulfonic acid (pTSA), 2-hydroxypropane-2-sulfonic acid, 2,4,6-trimethylbenzenesulfonic acid or dodecylsulfonic acid. The Brønsted acid used is preferably sulfuric acid or a sulfonic acid, more preferably sulfuric acid. Metal or compounds thereof may also be used, for example tin powder, tin(II) oxide, tin(II) oxalate, titanic esters such as tetraisopropyl orthotitanate or tetrabutyl orthotitanate and also zirconium esters such as tetrabutyl zirconate and also sodium methoxide and potassium methoxide.

Suitable Lewis acids for the transesterification in step d) are titanium(IV) isopropoxide, $Bu_2SnO$, $BuSn(O)OH$ or aluminium triflate. Preference is given to using titanium(IV) isopropoxide and aluminium triflate as Lewis acids.

Suitable bases for the transesterification in step d) are alkali metals, alkali metal alkoxides, alkali metal or alkaline earth metal acetates or oxides, alkali metal or alkaline earth metal alkoxides such as NaEtOH or MgEtOH, or alkali metal carbonates such as $K_2CO_3$ or $Cs_2CO_3$. Basic ion exchangers or NaOH may, however, also be used. Preference is given to using Na or Mg alkoxides such as NaEtOH or MgEtOH.

The acid-catalyzed transesterification is preferably carried out at a temperature from 60 to 220° C., more preferably from 100 to 210° C. and particularly preferably at 130 to 200° C. The reaction preferably takes place above the boiling point of the first alcohol to be eliminated so as to remove the eliminated first alcohol directly from the reaction mixture and thus promote a shift in equilibrium to the product side. The second alcohol is preferably added to the ester formed in step a) in a significant excess, for example 30:1.

The base-catalyzed transesterification takes place preferably at a temperature of 20 to 100° C.

The described transesterification affords a second product mixture comprising at least the ester with the second alcohol, the eliminated first alcohol and unreacted second alcohols.

The second ester formed in step d) is separated from the remaining second product mixture in the subsequent step e). The separation is carried out by means of a thermal separation, preferably distillation, and/or by means of membrane separation, in particular using the membrane materials described above. The appropriate process conditions are known to those skilled in the art.

In the separation process used in step e) and in the distillation in particular, there is the possibility that this separates from the rest of the second product mixture not just the ester formed, but high boilers that have possibly formed too, for example high-boiling by-products that can arise in the reaction in step c1). In order to remove these high boilers, the process according to the invention may include a purification step, i.e. a step in which the ester formed in step c1) is purified by separating the ester from the high boilers present by means of a thermal separation, extraction, crystallization or membrane separation. Preferably a thermal separation process, more preferably a further distillation, is used to purify the esters formed. The process conditions are known to those skilled in the art.

The esters obtained according to the invention may serve as reactants for the production of further products. Important reactions of the esters obtained are hydrogenation to form alcohols, hydrolysis or saponification to form respectively carboxylic acids or carboxylic acid salts or aminolysis to form amides.

EXAMPLES

MET Cells (Batch Mode):

The tests were carried out in a commercially available dead-end batch-filtration cell of the METcell model from Evonik MET with the commercially available membranes listed in tables 1-3 and the PEEK-acetone membrane according to the invention. The PEEK-acetone membrane according to the invention was produced in accordance with the publication J. da Silva Burgal et al.; Journal of Membrane Science, vol. 479 (2015), pp. 105-116 (see also WO 2015/110843 A1).

Tests were carried out under the following conditions: 56.7 cm² active membrane surface area, 20 bar transmembrane pressure, 25° C. separation temperature (at 50° C. for PEEK), 250 rpm stirrer speed.

For determination of the retention, the marker 4,4'-di-tert-butyl-2,2'-dipyridyl was added to the test mixture in a content of 0.01% by weight. The specified marker was chosen as one having the structure and molecular mass that are representative of ligands typically used in methoxycarbonylation (for example EP 3 121 186 A2) and corresponding to catalytic amounts at low concentration. In addition, 0.5% by weight of aluminium triflate (based on the total weight of the mixture) was added as the acid.

The METcell was filled with 200 ml of the above-described mixture and brought to the operating temperature (=separation temperature). It was then pressurized with nitrogen to an operating pressure of 20 bar. A total of 100 ml was withdrawn from the METcell as permeate, the permeate weight being continuously recorded. At the end of the test, i.e. once 100 ml of permeate had been withdrawn from the METcell, samples of the retentate and permeate were taken for GC and HPLC analyses. The reported permeability is an average across the 100 ml of permeate collected (results: table 1).

The retention was determined by HPLC-UV on a C18 column (results: see table 2) and alcohol selectivity by GC-FID (results: see table 3). The processes are known to those skilled in the art.

Example 1

Various membrane materials were investigated with a mixture consisting of 43% by weight of methanol and 57% by weight of methyl octanoate, which corresponds to a molar ratio of 4:1. As mentioned, the mixture additionally contained the marker (0.01% by weight of 4,4'-di-tert-butyl-2,2'-dipyridyl) and the acid (0.5% by weight of aluminium triflate).

TABLE 1

Comparison of permeability

| Membrane | $P_{t=0}$ | $P_{t=70h}$ | $P_{t=300h}$ | $P_{rel\ t=70h}$ | $P_{rel\ t=300h}$ |
| --- | --- | --- | --- | --- | --- |
| | kg/m²h¹bar¹ | | | % | |
| GMT oNF-2 | 0.6 | 1.63 | —* | 272 | —* |
| Evonik DuraMem 300 | 0.09 | ** | 0.44 | ** | 489 |
| Evonik PuraMem S | 0.68 | 1.95 | 10.65 | 287 | 1566 |
| PEEK | 0.23 | 0.27 | 0.28 | 117 | 122 |
| Solsep NF 010206 S | 0.32 | 0.70 | 0.84 | 219 | 263 |
| Solsep NF 030306 F | 0.15 | 0.31 | 0.38 | 207 | 253 |

*No data point, on account of material failure
**Data point not available

TABLE 1

Comparison of membrane retention (for the marker)

| Membrane | $R_{70h}$ | $R_{150h}$ | $R_{300h}$ |
| --- | --- | --- | --- |
| | % | | |
| GMT oNF-2 | 97 | 94 | —* |
| Evonik DuraMem 300 | 64 | ** | 59 |
| Evonik PuraMem S | 78 | 40 | 27 |

TABLE 1-continued

Comparison of membrane retention (for the marker)

| Membrane | $R_{70h}$ | $R_{150h}$ | $R_{300h}$ |
| --- | --- | --- | --- |
| | % | | |
| PEEK | 81*** | 77 | 80 |
| Solsep NF 010206 S | 39 | 24 | 5 |
| Solsep NF 030306 F | 90 | 60 | 59 |

*No data point, on account of material failure
**Data point not available
***Measured at 22 h

TABLE 3

Comparison of alcohol selectivities (shown here for methanol)

| | S for methanol | | |
| --- | --- | --- | --- |
| Membrane | $S_{70h}$ | $S_{150h}$ | $S_{300h}$ |
| GMT oNF-2 | 1.38 | 1.36 | —* |
| Evonik DuraMem 300 | 1.04 | ** | 1.18 |
| Evonik PuraMem S | 0.93 | 0.96 | 0.92 |
| PEEK | 0.81 | 0.72 | 0.71 |
| Solsep NF 010206 S | 1.1 | 1.09 | 1.00 |
| Solsep NF 030306 F | 1.23 | 1.22 | 1.17 |

*No data point, on account of material failure
**Data point not available

The tables show that the comparative examples for the DuraMem 300 and PuraMem S membranes exhibit a sometimes extreme increase in permeability over time. With the PuraMem S, it was established from the membrane retention that the membrane material had lost its technical integrity over time. By contrast, the DuraMem 300 showed relatively constant retention values, but after 300 hours showed an unacceptable increase in permeability and was accordingly then no longer very selective for the retention of methanol. The GMT oNF-2 membrane did not last 300 hours, but perished as a consequence of inadequate acid stability. The Solsep NF 010206 S membrane showed an unacceptable increase in permeability after just 70 hours and in any case also showed no particular selectivity (~1) for methanol. The Solsep NF 030306 F membrane showed values >1 for selectivity for methanol and therefore shows no selectivity for methanol. An unacceptable increase in permeability was also observed for this membrane.

By contrast, the PEEK-acetone membrane according to the invention shows good permeability even after 300 hours, with this increasing only slightly, and also good retention and good selectivity (<1) for methanol. Methanol is thus enriched in the retentate too.

Example 2

PEEK membranes were investigated with mixtures of various alcohols and esters. The mixture additionally contained the marker (0.01% by weight of 4,4'-di-tert-butyl-2,2'-dipyridyl) and the acid (0.5% by weight of aluminium triflate) already mentioned in example 1. In analogous manner to example 1, esters and alcohols were used in a molar ratio such that approximately 4 alcohol groups per ester group were always present, i.e. the molar ratio was in each case adjusted according to the number of functional groups. The investigations were carried out with the esters methyl propionate, isopropyl propionate, methyl tetradecanoate, octyl butyrate, octyl octanoate, octyl isovalerate and benzyl propionate, the diester dimethyl adipate and the alcohols methanol, isopropanol, octanol, benzyl alcohol and 2-ethylhexanol. The esters chosen were ones consisting of olefins of varying chain length and varying numbers of olefinic double bonds. In addition, the esters were varied in respect of potential alcohols (C1-C8). The tests were carried out under the following conditions: 56.7 cm² active membrane surface area, 40 bar transmembrane pressure, 50° C. separation temperature, 250 rpm stirrer speed.

TABLE 4

Comparison of alcohol selectivities using PEEK membranes

| Mixture<br>Alcohol/ester | S for the alcohol used | | |
|---|---|---|---|
| | $S_{0h}$ | $S_{150h}$ | $S_{300h}$ |
| Methyl propionate/methanol | 0.93 | 0.92 | 0.94 |
| Isopropyl propionate/isopropanol | 0.93 | 0.91 | 0.93 |
| Methyl tetradecanoate/methanol | 1.01 | 0.86 | ** |
| Octyl butyrate/octanol | 0.92 | 0.92 | 0.95 |
| Octyl octanoate/octanol | 0.92 | 0.88 | 0.93 |
| Octyl isovalerate/octanol | 0.95 | 0.94 | 0.94 |
| Benzyl propionate/benzyl alcohol | 0.98 | 0.99 | 0.99 |
| Dimethyl adipate/methanol | 0.98 | ** | 0.97 |

**No data point available

It was found out that good selectivities can be achieved for the alcohols employed, even when using different alcohols and different esters.

TABLE 5

Comparison of membrane retention (for the marker) using PEEK membranes

| Mixture<br>Alcohol/ester | $R_{0h}$ | $R_{150h}$<br>% | $R_{300h}$ |
|---|---|---|---|
| Methyl propionate/methanol | 97 | 97 | 97 |
| Isopropyl propionate/isopropanol | 99 | 99 | 99 |
| Methyl tetradecanoate/methanol | 86 | 85 | ** |
| Octyl butyrate/octanol | 99.9 | 97 | 97 |
| Octyl octanoate/octanol | 95 | 97 | 97 |
| Octyl isovalerate/octanol | *** | *** | *** |
| Benzyl propionate/benzyl alcohol | *** | *** | *** |
| Dimethyl adipate/methanol | 89 | ** | 88 |

**No data point available
***Data point not yet available

It was likewise found out that good results for membrane retention were achieved over time for the marker for all alcohol-ester mixtures used.

TABLE 6

Comparison of permeability using PEEK membranes

| Mixture<br>Alcohol/ester | $P_{t=0}$ | $P_{t=150h}$<br>L/m²h¹bar¹ | $P_{t=300h}$ |
|---|---|---|---|
| Methyl propionate/methanol | 0.065 | 0.063 | 0.063 |
| Isopropyl propionate/isopropanol | 0.031 | 0.033 | 0.036 |
| Methyl tetradecanoate/methanol | 0.035 | 0.054 | ** |
| Octyl butyrate/octanol | 0.008 | 0.008 | 0.010 |
| Octyl octanoate/octanol | 0.005 | 0.006 | 0.009 |
| Octyl isovalerate/octanol | 0.014 | 0.016 | 0.015 |
| Benzyl propionate/benzyl alcohol | 0.199 | 0.204 | 0.168 |
| Dimethyl adipate/methanol | 0.026 | ** | 0.028 |

**No data point available

Some of the permeabilities are very low, which is a consequence for example of the relatively long chains of carbon atoms or of the size of the molecule in general. Despite the low permeability, good retentions (for the marker) and good selectivities (for methanol) were achieved. Furthermore, it can be seen from the table that the permeability does not rise substantially over 300 h.

Example 3: Testing in Triplicate (Continuous Mode)

The tests were carried out in a continuously operated test system with complete recycling of the permeate in a closed loop. The system essentially comprises a high-pressure through-flow loop pressurizable up to 60 bar having three flat-channel membrane cells. The loop is fed from a reservoir with a capacity of 5 L filled with a feed solution that is mechanically mixed and blanketed with nitrogen. A diaphragm piston pump is used to bring the feed solution to the operating pressure of the membrane loop and thus to the high-pressure region of the test system. The high-pressure region of the test system consists essentially of a liquid loop, which is operated by means of a circulation pump, and three flat-membrane test cells and also the necessary sensors (e.g. pressure measurement, measurement of through-flow volume in the loop). The liquid flow penetrating through the membrane is withdrawn from the membrane modules as permeate and recycled into the reservoir. The amount of permeate is continuously recorded for all three membranes in accordance with the Coriolis measurement principle. Circulation in the high-pressure loop is by means of a centrifugal pump in order to ensure the required through-flow across the membranes. The through-flow is normally set sufficiently high such that the concentrations on the feed side and retentate side of the membrane are approximately equal. (This is the case if the through-flow volume substantially exceeds the discharged permeate stream.) The feed rate to the high-pressure loop via the high-pressure pump is likewise chosen such that the volume flow of the feed stream exceeds the volume flow of the permeate many times over. The excess feed volume (supply stream to the high-pressure pump minus the total permeate of the three membranes) is likewise recycled into the reservoir. This recycling is effected by means of a mechanical supply pressure regulator, which is also used to set the supply pressure for the nanofiltration stage. The loop is heated by means of a thermostat in order to ensure a defined temperature for the separation. The tests were carried out under the following conditions: active membrane surface area per module 84.5 cm², transmembrane pressure 20 bar, separation temperature 40° C.

Various membrane materials were investigated with a mixture of 43% by weight of methanol and 57% by weight of methyl octanoate (molar ratio 4:1). To determine the retention, the marker 4,4'-di-tert-butyl-2,2'-dipyridyl was added to the test mixture in a content of 0.01% by weight, as in the previous examples. In addition, 0.5% by weight of aluminium triflate (based on the total weight of the mixture) was added after a defined operating time. The time of acid addition is defined in the tables 7 to 9 below as time t=0 h. At the defined sampling times, liquid samples of the respective permeate streams, of the feed and of the retentate were collected.

The permeability was determined as described above (results in table 7). The retention of the marker was determined by HPLC with UV detector (260 nm) on a C18 column (results in table 8) and the alcohol selectivity was determined by GC with FID detector (results in table 9).

TABLE 7

Comparison of permeability

| Membrane | $P_{t=0h}$ $L/m^2h^1bar^1$ | $P_{t=100h}$ | $P_{rel\ t=100h}$ % |
|---|---|---|---|
| PEEK | 0.21 | 0.21 | 100 |
| GMT oNF2 | 5.59 | —* | —* |
| SolSep 030306F | 0.59 | 1.36 | 244 |
| SolSep NF030306 | 0.79 | 0.96 | 120 |
| SolSep NF030705 | 1.86 | 6.96 | 377 |
| SolSep NF030105 | 2.58 | 8.22 | 329 |

*No data point, on account of material failure

TABLE 8

Comparison of membrane retention

| Membrane | $R_{t=50h}$ | $R_{t=100h}$ % |
|---|---|---|
| PEEK | 93.3 | 93.5 |
| GMT oNF2 | —* | —* |
| SolSep 030306F | 41.3 | 45.3 |
| SolSep NF030306 | 62.5 | 67.7 |
| SolSep NF030705 | 14 | 14.7 |
| SolSep NF030105 | 49.9 | 56.3 |

*No data point, on account of material failure

TABLE 9

Comparison of alcohol selectivities
(shown here for methanol)

| | S for methanol % | |
|---|---|---|
| Membrane | $S_{t=50h}$ | $S_{t=100h}$ |
| PEEK | 0.9 | 0.9 |
| GMT oNF2 | —* | —* |
| SolSep 030306F | 1.09 | 1.11 |
| SolSep NF030306 | 1.16 | 1.19 |
| SolSep NF030705 | 1.03 | 1.05 |
| SolSep NF030105 | 1.05 | 1.08 |

*No data point, on account of material failure

The GMT oNF-2 membrane did not last 300 hours, but perished as a consequence of inadequate acid stability. All Solsep membranes showed an unacceptable increase in permeability after just 100 hours and in any case also showed no particular selectivity for methanol, but instead showed selectivity values >1 for methanol, which means that methanol passes through the membrane preferentially and is not retained. It was therefore not possible to achieve the object of the invention with the Solsep membranes. By contrast, the PEEK membrane according to the invention shows good permeability even after 100 hours, with this increasing only slightly, and also good retention and good selectivity (<1) for methanol. Methanol is thus enriched in the retentate too.

Example 4

Conversion of diisobutene (DiB) to methyl 3,5,5-trimethylhexanoate (TMH ester) with membrane separation as catalyst recycling DiB is a mixture consisting of the two C8 isomers 2,4,4-trimethylpent-1-ene and 2,4,4-trimethylpent-2-ene in ratios of about 80:20. The tests were carried out in a continuously operated test system with the setup described below.

The system essentially comprises a 200 ml glass autoclave (=reactor) from Büchi (pressurizable up to 10 bar). The autoclave is fed by means of Knauer HPLC pumps from a glass reservoir filled with reaction solution and blanketed with argon. A further Knauer HPLC pump is used to pump from the glass autoclave into the separate high-pressure loop, which is pressurizable up to 60 bar. The high-pressure loop of the test system consists essentially of a liquid loop, which is operated by means of a circulation pump, and a flat-membrane test cell and also the necessary sensors (e.g. pressure measurement, measurement of temperature). Circulation in the high-pressure loop is by means of a centrifugal pump in order to ensure the required through-flow across the membranes. The liquid stream penetrating through the membrane is withdrawn from the membrane module as permeate and collected in an argon-blanketed glass receiver. The permeate rate is continuously recorded by means of a balance. The excess feed volume (retentate) is recycled into the glass autoclave. This recycling is effected by means of a mechanical supply pressure regulator, which is also used to set the supply pressure for the nanofiltration stage. The loop is heated by means of a thermostat in order to ensure a defined temperature for the separation. The tests were carried out under the following conditions: active membrane surface area 84.5 cm$^2$, transmembrane pressure 45 bar, separation temperature 25° C.

It is possible to take samples of the feed stream to the high-pressure loop (feed), from the high-pressure loop (retentate), and of the permeate. For analysis of the yield, 0.08 g of the sample and 0.03 g of ethylbenzene (internal standard) were weighed out and diluted with 0.25 g of acetonitrile The subsequent analysis was by GC-FID. The retention of ligands and metal was determined by ICP-OES after prior digestion of the samples of permeate and retentate. The analysis for the retention of acid was by $^{19}$F NMR.

Sample preparation and analysis for all three methods are known to those skilled in the art.

The membrane material used was PEEK. The PEEK-acetone membrane according to the invention was produced in accordance with the publication J. da Silva Burgal et al.; Journal of Membrane Science, vol. 479 (2015), pp. 105-116 (see also WO 2015/110843 A1).

The contents of the glass autoclave were stirred in order to ensure virtually ideal mixing. The pressure in the glass autoclave was adjusted to 10 bar by means of a mechanical supply pressure regulator. The glass autoclave is held at the desired temperature by means of an oil bath having an external temperature-measurement device mounted in the glass autoclave.

The glass autoclave and high-pressure loop were first filled with a base reaction mixture consisting of 56% by weight of MeOH, 40% by weight of DiB, 0.5% by weight of 1,2-bis((tert-butyl(pyridin-2-yl)phosphanyl)methyl)benzene (ligand), 3.4% by weight of aluminium triflate (acid) and 0.1% by weight of [Pd(acac)$_2$] (metal), inertized with argon at 10 bar and put into operation.

The glass autoclave was then heated to an internal temperature of 100° C. and the initial argon flow was changed to CO (start of reaction). Over the course of 15 h, the base reaction mixture was pumped in circulation to start up the system. After 15 h, 99% of the DiB in the feed had been converted into TMH ester. After 15 h, circulation mode was ended, and the permeate was collected in separate glass vessels and fresh reaction solution (60% by weight of MeOH and 40% by weight of DiB) was metered in. New permeate collecting vessels were used for the test periods listed in table 1. No fresh catalyst, ligand or acid was added over the test period of 105 h. For the respective test periods, the permeability, yield of the TMH ester and retentions for the components of the catalyst system were determined by the methods specified above.

TABLE 1

Continuous conversion of DiB into TMH ester

| Period h | Ti (glass autoclave) °C. | P kg/m²h¹bar¹ | Y (TMH ester) * % | R (metal) % | R (ligand) % | R (acid) % |
|---|---|---|---|---|---|---|
| 0-15 | 100 | 0.045 | 99 | | ** | |
| 15-35 | 100 | 0.051 | 84 | 98 | 97 | 97 |
| 35-70 | 90 | 0.049 | 73 | 97 | 98 | 96 |
| 70-90 | 80 | 0.050 | 59 | 98 | 97 | 97 |
| 90-105 | 100 | 0.048 | 84 | 97 | 98 | 96 |

*Yield at the end of the respective test period in each case.
**No retentions determined (startup of the system).

The invention claimed is:

1. An alkoxycarbonylation process for preparing an ester by carbonylation of a C2 to C16 alkene or isoalkene, wherein the alkoxycarbonylation process comprises the following steps:
   a) carbonylating a C2 to C16 alkene or isoalkene having at least one olefinic double bond with carbon monoxide and with an alcohol wherein the alcohol that is a mono- or polyol (two or more OH groups) have from 1 to 50 carbon atoms or is a mixture of two or more mono- and/or polyols and which, when it is a monool, is used in a molar ratio to the C2 to C16 hydrocarbon (alcohol: C2 to C16 hydrocarbon) of from 2 to 20 or which, when it is a polyol, is used in a molar ratio to the alkene or isoalkene used (alkene or isoalkene:polyol) of from 2 to 20, in the presence of a homogeneous catalyst system comprising at least one metal of groups from 8 to 10 of the periodic table of the elements or a compound thereof, a phosphorus-containing ligand and an acid, in a reaction zone of step a) to obtain a liquid product mixture that comprises at least the ester formed by the reaction, the homogeneous catalyst system, low boilers, high boilers and unreacted alcohols of step a);
   b) carrying out a membrane separation with a membrane material to separate the homogeneous catalyst system from the liquid product mixture, whereby the homogeneous catalyst system and unreacted alcohol of step a), are enriched in a retentate and the ester formed in step a) is enriched in a permeate,
   wherein the membrane material is an OSN (organic solvent nanofiltration) comprising a separation-active layer comprising a PEEK (polyether ether ketone) polymer, and a porous backing and the membrane material is stable in the presence of the acid of the catalyst system and not destroyed for at least 300 hours wherein the acid in the catalyst system is a Brønsted acid having a pKa <5 or a Lewis acid, and the membrane material has a membrane retention R for the ligand of the homogeneous catalyst system is at least 75%, and worsens by not more than 30 percentage points; or a relative permeability $P_{rel}$ value between 30% and 300%, and the retentate is recycled into the reaction zone and wherein on recycling the retentate, a purge stream is removed from the retentate;
   c) working up the permeate by means of one or more separation steps selected from thermal separation, extraction, crystallization or membrane separation, by means of one or more distillation steps, for removing the ester formed in step a) and for removing the unreacted C2 to C16 alkene or isoalkene having at least one olefinic double bond and/or the unreacted alcohol and recycling of the unreacted C2 to C16 alkene or isoalkene having at least one olefinic double bond and/or the unreacted alcohol of step a) into the reaction zone of step a);
   and wherein the molar ratio of the Bronsted acid to ligand is from 1:1 to 15:1, and the molar ratio of Lewis acid to ligand is from 1:1 to 20:1.

2. The alkoxycarbonylation process according to claim 1, wherein the membrane material has the following two characteristics:
   the membrane retention R for the ligand of the homogeneous catalyst system is at least 85%, and worsens by not more than 30 percentage points; or
   the relative permeability $P_{rel}$ has a value between 30% and 300%; and
   the acid in the catalyst system is selected from the group consisting of a Brønsted acid having a pKa <3 and a Lewis acid, wherein the molar ratio of the Bronsted acid to ligand is from 1:1 to 10:1, and the molar ratio of Lewis acid to ligand is from 2:1 to 15:1.

3. The alkoxycarbonylation process according to claim 1, wherein the PEEK polymer has a degree of sulfonation of less than 20%.

4. The alkoxycarbonylation process according to claim 3, wherein the PEEK polymer has a degree of sulfonation of less than 10%.

5. The alkoxycarbonylation process according to claim 1, wherein the alcohol used in step a) is selected from the group consisting of ethanol, 1-propanol, 1-butanol, 1-pentanol, 1-hexanol, 2-propanol, tert-butanol, and 3-pentanol.

6. The alkoxycarbonylation process according to claim 5, wherein the alcohol used in step a) is selected from the group consisting of ethanol, 1-propanol, 1-butanol, 1-pentanol, 1-hexanol, 2-propanol, tert-butanol, 3-pentanol, and 2-propylheptanol.

7. The alkoxycarbonylation process according to claim 1, wherein the C2 to C16 alkene or isoalkene having at least one olefinic double bond that is used in step a) is an n- or isoalkene having from 2 to 16 carbon atoms.

8. The alkoxycarbonylation process according to claim 1, wherein the metal of groups 8 to 10 of the periodic table of the elements or a compound thereof in the homogeneous catalyst system in step a) is palladium or a compound thereof.

9. The alkoxycarbonylation process according to claim 1, wherein the phosphorus ligand in the homogeneous catalyst system has a bidentate structure.

10. The alkoxycarbonylation process according to claim 1, wherein the acid in the catalyst system in step a) is a Brønsted acid having a pKa ≤5, or a Lewis acid having an LAU value of more than 25.

11. The alkoxycarbonylation process according to claim 1, wherein the acid in the catalyst system in step a) is a Brønsted acid or a Lewis acid, the Brønsted acid being perchloric acid, sulfuric acid, phosphoric acid, methylphosphonic acid or a sulfonic acid, and the Lewis acid being aluminium triflate, aluminium chloride, aluminium hydride, trimethylaluminium, tris(pentafluorophenyl)borane, boron trifluoride, boron trichloride or a mixture thereof.

12. The alkoxycarbonylation process according to claim 1, wherein the reaction zone of step a) includes at least one reactor.

13. The alkoxycarbonylation process according to claim 2, wherein the acid in the catalyst system in step a) is a Brønsted acid having a pKa ≤3, or a Lewis acid having an LAU value of more than 29,
wherein the molar ratio of the Bronsted acid to ligand is from 3:1 to 5:1, and the molar ratio of Lewis acid to ligand is from 5:1 to 10:1.

14. The alkoxycarbonylation process according to claim 1, wherein the membrane material according to the invention exhibits the following two characteristics:
the membrane retention R for the ligand of the homogeneous catalyst system is at least 85%, and worsens by not more than 20 percentage points; or
the relative permeability $P_{rel}$ has a value between 50% and 150%.

15. The alkoxycarbonylation process according to claim 1, wherein the membrane material according to the invention exhibits the following two characteristics:
the membrane retention R for the ligand of the homogeneous catalyst system is at least 90%, and worsens by not more than 10 percentage points; or
the relative permeability $P_{rel}$ has a value between 75% and 125%.

16. The alkoxycarbonylation process according to claim 1, wherein the acid in the catalyst system in step a) is a Brønsted acid having a pKa ≤3, or a Lewis acid having an LAU value of more than 29.

17. The alkoxycarbonylation process according to claim 2, wherein the PEEK polymer has a degree of sulfonation of less than 20%.

18. The alkoxycarbonylation process according to claim 17, wherein the PEEK polymer has a degree of sulfonation of less than 20%.

* * * * *